United States Patent [19]
Walker

[11] Patent Number: 5,609,270
[45] Date of Patent: Mar. 11, 1997

[54] DRIED BIOLOGICAL REAGENT PILL DISPENSER WITH VIBRATING MECHANISM

[75] Inventor: David W. Walker, Milwaukee, Wis.

[73] Assignee: Pharmacia Biotech, Inc., Milwaukee, Wis.

[21] Appl. No.: 563,163

[22] Filed: Nov. 27, 1995

[51] Int. Cl.$^6$ .................................................. B65G 59/00
[52] U.S. Cl. ........................... 221/202; 221/204; 221/266
[58] Field of Search .................................... 221/202, 203, 221/204, 263, 265, 266, 275; 222/233, 234, 268

[56] References Cited

U.S. PATENT DOCUMENTS

| | | |
|---|---|---|
| 1,013,674 | 1/1912 | Millard . |
| 1,120,500 | 12/1914 | Hughes . |
| 1,269,768 | 6/1918 | Whitener . |
| 1,980,859 | 6/1934 | Greve . |
| 2,188,304 | 1/1940 | Surdenik ................................. 221/275 |
| 2,256,340 | 5/1941 | Gora et al. . |
| 2,669,349 | 2/1954 | Silver .................................... 221/202 |
| 2,681,529 | 12/1954 | Braithwaite . |
| 4,638,923 | 1/1987 | Mines et al. ............................ 221/132 |
| 4,648,529 | 3/1987 | Blakemore et al. ........................ 221/1 |

FOREIGN PATENT DOCUMENTS

| | | | |
|---|---|---|---|
| 0484224 | 5/1992 | European Pat. Off. ................ | 221/202 |
| 602568 | 9/1934 | Germany ................................. | 221/266 |

*Primary Examiner*—H. Grant Skaggs
*Attorney, Agent, or Firm*—Quarles & Brady

[57] ABSTRACT

A dispenser include a housing with an inlet through which reagent pills are received from a vial. Within the housing is a dispensing tube that forms a pill passageway which has a first portion of relatively large cross section adjacent the inlet and a funnel portion in which the passageway reduces in cross section to a narrower linearizing portion. The dispensing tube has a series of ridges on an exterior surface. A metering shaft extends across the linearizing portion and has a depression for conveying one reagent pill at a time between sections of the linearizing portion when the metering shaft is rotated. A gear on the metering shaft is meshes with teeth on a plunger which is slidably mounted in the housing. The plunger also has a member projecting therefrom and against dispensing tube. A user pressing the plunger causes the metering shaft to rotate transferring a reagent pill to a portion of the passageway connected to the outlet of the housing and thereby ejects that reagent pill from the housing. That plunger movement also causes the member to ride over the ridges which vibrates the dispensing tube loosening any pills that become jammed in the funnel portion.

6 Claims, 3 Drawing Sheets

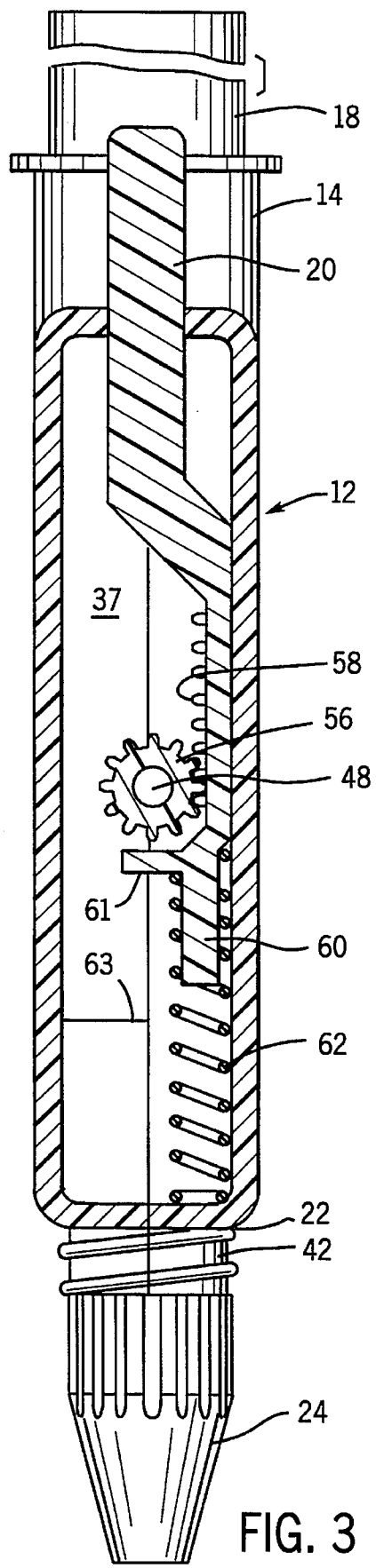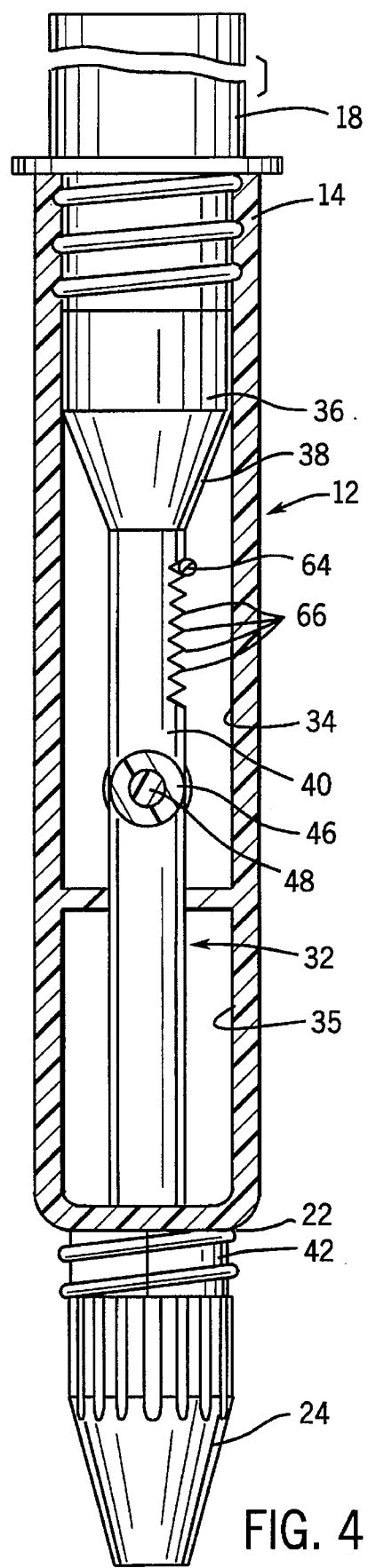

DRIED BIOLOGICAL REAGENT PILL DISPENSER WITH VIBRATING MECHANISM

BACKGROUND OF THE INVENTION

The present invention relates to apparatus for dispensing biological materials and reagents; and more particularly to apparatus for dispensing individual glassy, porous reagent pills into a laboratory vessel in which a reaction is to take place.

Few biologically active materials are sufficiently stable so that they can be isolated, purified, and then stored in solution at room temperature. As a consequence biological reagents often are provided in dried form to increase their storage stability. In preparing reagents for convenient and efficient testing of biological samples, it is frequently important to obtain dry chemical blends in uniform, discreet amounts. These reagents must be efficiently and economically prepared in small, precisely measured quantities for laboratory use.

One type of carrier which has been used to stabilize doses of biological reagents are glass-forming filler materials, such as a sucrose polymer. A measured amount of a biological reagent solution is incorporated into the filler material, which is a water-soluble or water-absorbing substance. The composite then is freeze dried to produce a sphere shaped reagent pill having a composition which immobilizes and stabilizes the biological reagent. Examples of glass-forming filler materials for stabilizing biological reagents are described in F. Franks, "Long-Term Stabilization of Biologicals", 12 *Bio-Technology* 253 (1994); U.S. Pat. No. 5,098,893; U.S. Pat. No. 5,200,399 and U.S. Pat. No. 5,240,843.

The biological reagent pills must be kept relatively dry during storage. Otherwise, moisture allows the filler material to change into a rubber state which causes the reagent contained therein to become unstable. As a consequence, reagent pills must be stored in a container that is sealed against moisture.

To use the reagent in a biological procedure or experiment, the carrier pills have to be individually dispensed from the storage container. In order to dispense a single pill at a time, the dispenser has to organize the pills contained in a storage vessel into a stream that is one pill wide. A funnel can be used for this purpose, but spherical the pills tend to jam in the conical bottom thereby blocking the outlet. In addition, dried reagent pills easily become charged with static electricity which causes them to cling to the walls of conventional dispensing apparatus.

SUMMARY OF THE INVENTION

The general object of the present invention is to provide a dispenser for reagent pills containing biological material.

Another object is to provide such a dispenser with a mechanism that preventing the pills from jamming and clinging to the interior walls.

A further object of the present invention is to provide a dispenser which can be held in and easily operated with one hand of a user to eject individual reagent pills directly into laboratory vessels.

These and other objectives are fulfilled by an apparatus which includes a body preferably formed of an electrically conductive material. The body comprises a housing with a tube therein that forms a passageway for the reagent pills being dispensed. The housing has a size and shape that can be held easily in a user's hand and provides an inlet for receiving the reagent pills from a vial. A metering shaft projects transversely through the tube dividing the passageway into two sections. A depression is provided in the metering shaft to convey one pill at a time between the two passageway sections upon rotation of the metering shaft.

A plunger is slidably mounted to the housing and is coupled by a transmission to the metering shaft whereby sliding movement of the plunger produces rotation of the metering shaft. In the preferred embodiment, the transmission comprises teeth on the plunger and a gear connected to the metering shaft in engagement with the plunger teeth. A spring biases the plunger into a normal operating position.

A member extends between the plunger and the tube to vibrate the tube as the plunger moves. In the preferred embodiment, the exterior surface of the tube has a plurality of ridges, such as regularly spaced teeth. The member is attached to and projects from the plunger in abutment with the ridges. As the plunger slides with respect to the housing, the member rides over the ridges producing a washboard effect that vibrates the tube thereby shaking loose any pills that are jammed therein.

BRIEF DESCRIPTION OF THE DRAWINGS

FIG. 3 is a cross section view taken along line 3—3 in FIG. 1;

FIG. 4 is a cross section view taken along line 4—4 in FIG. 3.

DETAILED DESCRIPTION OF THE INVENTION

Figure 1:
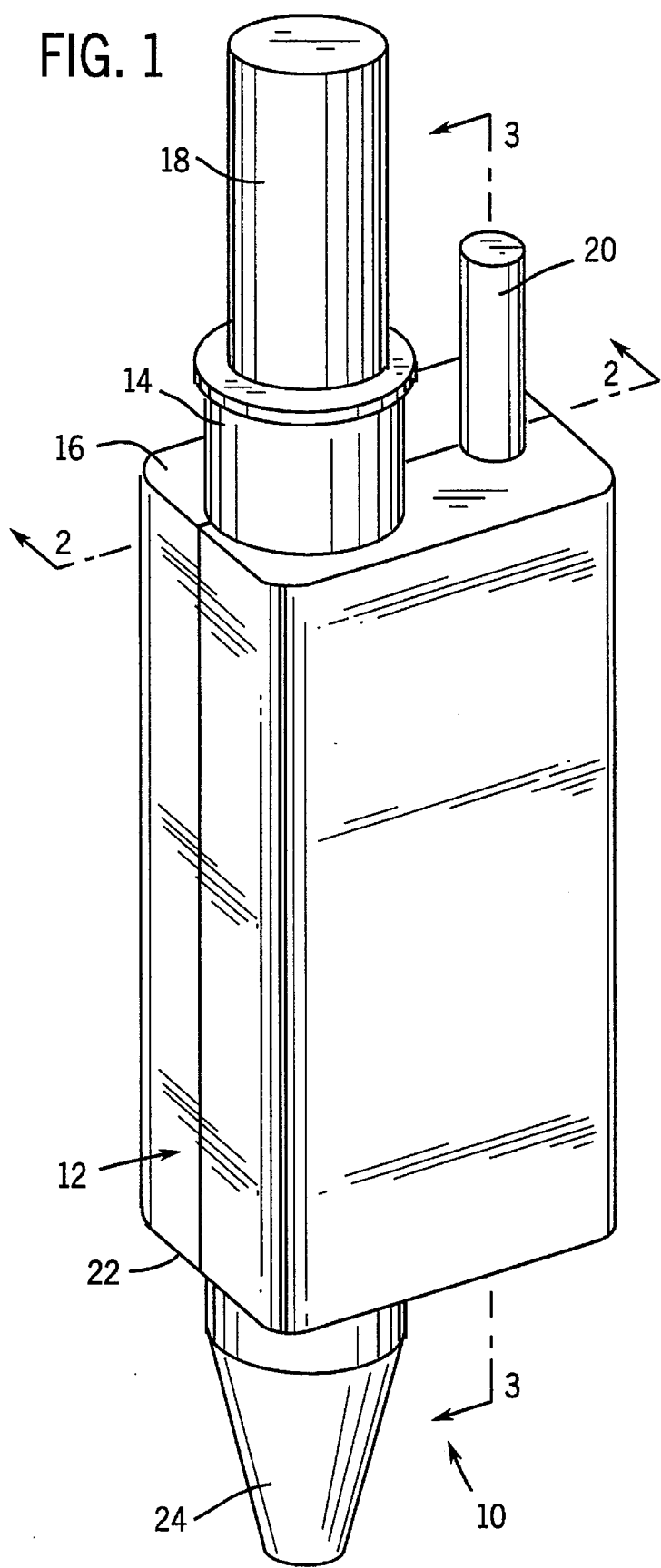
FIG. 1 is an isometric view of a dispenser according to the present invention.

With initial reference to FIG. 1, a dispenser 10 has a housing 12 forms a generally rectilinear body. A cylindrical coupling 14 projects from a first end 16 of housing 12 and has an opening in which to attach a vial 18 to the dispenser. The vial 18 is of the type commonly used by manufacturers to ship freezedried pills containing a biological reagent or other material to be dispensed. The first end 16 of the housing 12 also has a plunger 20 extending therefrom for activating the dispenser, as will be described. The opposite, or second, end 22 of housing 12 has an another opening with a conical shaped nozzle 24 attached thereto which forms a dispenser outlet through which the reagent pills are ejected.

Figure 2:
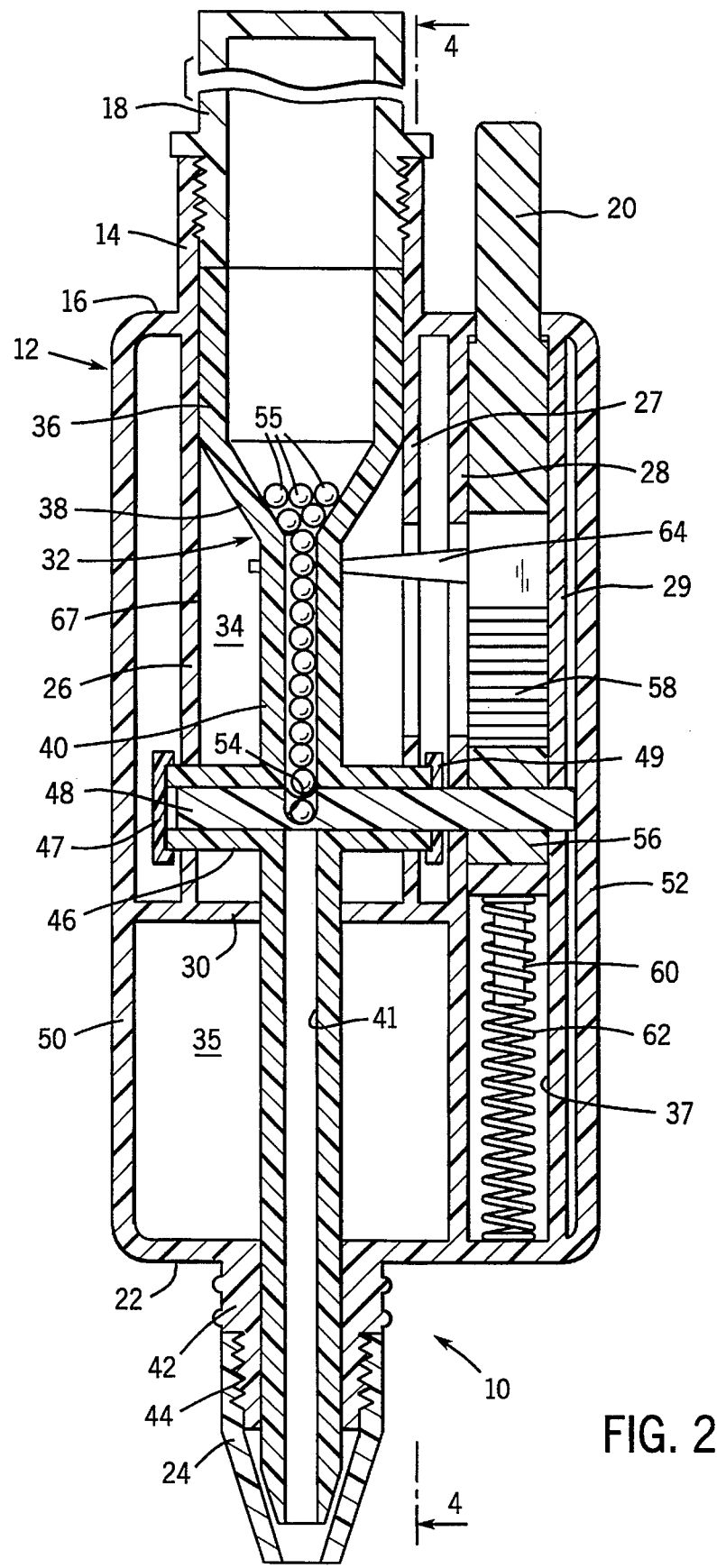
FIG. 2 is a cross section view taken along line 2—2 in FIG. 1.

Referring to FIG. 2, the housing 12 has a hollow interior which is subdivided by a plurality of walls 26, 27, 28, 29 and 30 into a number of internal chambers 34, 35 and 37. A dispensing tube 32 has a wide mouth section 36 located within one such chamber 34 between walls 26 and 27, with the wide mouth section opening into the interior of the cylindrical coupling 14. The opposite end of wide mouth section 36 is connected by a tapering, or funnel-like, section 38 to a narrower linearizing section 40 of the dispensing tube 32. Linearizing section 40 continues through the housing 12, exiting via an aperture in the other end 22. Upon exiting, the linearizing section 40 of the dispensing tube 32 passes through a column 42 having a reduced diameter portion with external screw threads 44 that engage internal screw threads on the nozzle 24. The nozzle is disposable and may be replaced after dispensing reagent pills for a given laboratory procedure to prevent cross contamination between different experiments.

The dispensing tube 32 has a cross tube 46 extending transversely across the linearizing section 40 between the interior housing walls 26 and 27. A metering shaft 48 extends through the cross tube 46 and outward toward one exterior side wall 52 of the dispenser 10. A first cap 47 provides an air-tight seal for the end of the cross tube 46 that is adjacent to the other exterior side wall 50 of the dispenser 10. An annular second cap 49 provides an air-tight seal at the other end of the cross tube through which the metering shaft 48 exits. The metering shaft 48 has a depression 54 therein which is aligned with the inner passageway 41 through the linearizing section 40 of the dispensing tube 32. The diameter and depth of the depression 54 is sufficient to receive only one of the spherical reagent pills 55 contained within the dispensing tube 32. As will be described, rotation of the metering shaft 48 carries the received reagent pill between upper and lower portions of the linearizing section 40, as will be described.

One end of the metering shaft 48 protrudes into the housing chamber 37 formed between interior walls 28 and 29. As shown in FIGS. 2 and 3, a gear 56 is securely attached to the metering shaft between walls 28 and 29 and meshes teeth 58 on the surface of plunger 20. The interior end of the plunger 20 has a shaft 60 projecting therefrom into a compression spring 62 that extends between the plunger and the interior surface at the second end 22 of the housing 12.

Referring to FIGS. 2 and 4, a rod 64 projects laterally inward from the plunger 20 passing to one side of the dispensing tube 32. The surface of that side of the dispensing tube 32 has a plurality of horizontal, triangular notches cut therein to form a series of ridges 66. The rod 64 fits within a depression between adjacent triangular ridges 66 as illustrated in FIG. 4.

As noted previously, the freeze-dried reagent pills become charged with static electricity. Therefore, to prevent those pills from clinging to the walls of the dispenser 10 due to that charge, components of the dispenser which come into contact with the reagent pills and the housing 12 are made of an electrically conductive material to dissipate the static electrical charge. For example, those components can be formed of a carbon filled plastic, such as a polycarbonate, although a metal filled plastic or metal housing also could be employed.

In order to use the present dispenser 10, the housing 12 is inverted so that the first end 16 is facing downward. An open vial 18 containing the freeze-dried reagent pills is screwed into the opening on the end of the dispenser coupling 14. The internal screw threads on the dispenser coupling 14 match the pitch of the screw threads on the vial 18. Different biological reagents can be distributed in vials having differing diameters and thread pitches with similarly configured openings in the dispenser coupling 14. Thus, a specific dispenser can be designed for use with a specific biological reagent and cannot be used with other biological materials shipped in different sized vials.

The dispenser housing 12 then is turned over which causes the reagent pills 55 within the vial 18 to fall downward into the dispensing tube 32, as shown in FIG. 2. The pills 55 are funneled by the tapering section 38 of the dispensing tube 32 into the narrower linearizing section 40. As previously note, the passageway 41 through the linearizing section is slightly greater than the largest diameter of a spherically shaped pill that is to be dispensed. Thus, only one pill at a time can pass from the tapering section 38 into the passageway 41 and the pills 55 become stacked therein above the metering shaft 48.

The force exerted by spring 62 pushes the plunger 20 into the upward position shown in the drawings. In that position, the teeth 58 on plunger 20 rotate the gear 56 and metering shaft 48 into a position at which the shaft's depression 54 is facing vial 18. This allows one of the reagent pills 55 in the linearizing section 40 to drop into the depression 54 as illustrated.

The user then positions the nozzle 24 over a test tube or other laboratory vessel into which a reagent pill is to be dispensed. The plunger 20 is pressed into the housing 12 which action causes the plunger teeth 58 to rotate the gear 56 and metering shaft 48 within the housing. The reagent pill that nests inside depression 54 moves with the metering shaft 48 within the passageway 41 through the dispensing tube 32. The length of travel of plunger 20 within the housing 12 is limited by tab 61 on the plunger striking an internal housing wall 63 shown in FIG. 3. The length of plunger travel and the number of teeth 58 are such that movement of the plunger 20 between extreme outward and inward positions causes a 180 degree rotation of the metering shaft 48 between positions at which depression 54 opens upward and downward in the orientation of a device shown in the drawings. As the metering shaft 48 rotates, its curved outer surface gently pushes the second lowest reagent pill upward within the dispensing tube passageway 41. These physical characteristics of the metering shaft 48 prevent the second lowest reagent pill from being sheared or crushed during the dispensing operation.

The downward facing position of depression 54 at the extreme inward depression of the plunger 20 allows the captivated reagent pill to drop downward, continuing through the interior passageway 41 of the dispensing tube 32 and falling out of the dispenser through the nozzle 24. Because the depression 54 is sized to accommodate only a single reagent pill at a time, each operation of the plunger 20 permits only a single pill to be ejected through the nozzle 24.

The downward movement of plunger 20 causes its lateral rod 64 to travel along the triangular ridges 66 on the dispensing tube 32 as apparent from the view in FIG. 4. This movement creates a "washboard" vibrational effect as the lateral rod 64 rides over the peaks of the ridges 66 and into the depressions between those ridges. This causes the linearizing section 40 of the dispensing tube 32 to vibrate which jiggles the pills 55 in the funnel section 38. The vibrations dislodge any pills 55 which are jammed in the funnel section 38 allowing the pills to drop downward into the linearizing section 40.

Once a reagent pill has been ejected, the user releases the plunger 20 which returns to the extended position due to the force of spring 62. This action also causes the plunger's lateral rod 64 to travel along the ridges 66 producing additional vibration of the dispensing tube 32 to dislodge jammed pills. If the dispenser 10 is continued to be held upright as illustrated, another reagent pill 55 within the dispensing tube passageway 41 drops into the depression 54 when the metering shaft 48 returns to the normal position, as shown in the drawings.

When the use of the dispenser 10 is complete, a cap (not shown) can be placed over the nozzle 24 sealing that opening of the dispenser. Alternatively, the user may invert the dispenser thereby causing the freeze-dried reagent pills 55 within the dispensing tube 32 to fall into the vial 18 which then can be unscrewed from the dispenser coupling 14 and sealed with a cap.

I claim:

1. A pill dispensing apparatus comprising:

a housing having an inlet through which the pills are received, and having an outlet;

a tube forming a passageway within said housing through which the pills pass between the inlet and the outlet;

a metering element dividing the passageway into two sections and having a depression for conveying a predefined number of pills at a time between the two sections upon movement of said metering element;

a plunger slidably mounted to said housing;

a transmission coupling said plunger to said metering element wherein movement of the plunger causes movement of said metering element; and a member engaging said plunger and said tube so as to transfer movement of said plunger to said tube in order to loosen pills that become jammed in said tube.

2. The apparatus as recited in claim 1 further comprising a spring which biases said plunger with respect to said housing.

3. The apparatus as recited in claim 1 wherein said tube comprises a first portion with an opening in communication with the inlet of said housing, a second portion in which the passageway has a smaller cross sectional area than in the first portion, and an intermediate portion between the first and second portion wherein the passageway tapers in cross-sectional area.

4. The apparatus as recited in claim 3 wherein said tube has an exterior surface with a plurality of ridges; and said member is attached to said plunger and rides across the ridges with movement of said plunger.

5. The apparatus as recited in claim 1 wherein said tube has an exterior surface with a plurality of ridges; and said member is attached to said plunger and rides across the ridges with movement of said plunger.

6. An apparatus for dispensing biological reagent pills from a vial, said apparatus comprising:

a housing having a first opening through which reagent pills are received from the vial and a second opening through which reagent pills are dispensed from the apparatus; and a dispensing tube forming a passageway within said housing for a reagent pill to pass through, and having a first section with an opening in communication with the first opening of said housing, a second section in which the passageway has a smaller cross section area than in the first section, the second section including a cross tube which has a passage therethrough in communication with the passageway, said dispensing tube having an exterior surface with a plurality of ridges;

a metering shaft extending into the cross tube and having a depression for conveying one reagent pill at a time between portion of the passageway on opposite sides of the cross tube, such conveying occurring upon rotation of said metering shaft;

a gear attached to said metering shaft and having teeth;

a plunger slidably mounted within and projecting from said housing and having a plurality of teeth meshed with the teeth of said gear wherein sliding of said plunger within the housing rotates said gear and said metering shaft, said plunger having a member extending therefrom wherein the member rides across the ridges upon movement of said plunger to produce movement of said dispensing tube; and a spring which biases said plunger.

* * * * *